US007089055B2

(12) United States Patent
Cates et al.

(10) Patent No.: US 7,089,055 B2
(45) Date of Patent: Aug. 8, 2006

(54) METHOD AND APPARATUS FOR DELIVERING PRE-SHOCK DEFIBRILLATION THERAPY

(75) Inventors: Adam W. Cates, Minneapolis, MN (US); Eric G. Lovett, Roseville, MN (US); Douglas J. Lang, Arden Hills, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 577 days.

(21) Appl. No.: 10/184,019

(22) Filed: Jun. 28, 2002

(65) Prior Publication Data

US 2004/0002739 A1 Jan. 1, 2004

(51) Int. Cl.
*A61N 1/36* (2006.01)
*A61N 1/39* (2006.01)

(52) U.S. Cl. .................... 607/4; 607/5; 607/14

(58) Field of Classification Search ............. 607/2–5, 607/9, 14, 46, 119, 120, 122
See application file for complete search history.

(56) References Cited

U.S. PATENT DOCUMENTS

| 3,692,027 A | 9/1972 | Ellinwood, Jr. ............. 128/260 |
| 4,003,379 A | 1/1977 | Ellinwood, Jr. ............. 128/260 |
| 4,146,029 A | 3/1979 | Ellinwood, Jr. ............. 128/260 |
| 4,271,192 A | 6/1981 | Wurtman et al. ............ 424/319 |
| 4,281,664 A | 8/1981 | Duggan ....................... 128/696 |
| 4,299,220 A | 11/1981 | Dorman ....................... 128/260 |
| 4,417,038 A | 11/1983 | Vogel et al. |
| 4,470,987 A | 9/1984 | Wurtman et al. ............ 424/259 |
| 4,544,371 A | 10/1985 | Dormandy, Jr. et al. .... 604/891 |
| 4,556,063 A | 12/1985 | Thompson et al. .... 128/419 PT |
| 4,559,946 A | 12/1985 | Mower ..................... 128/419 D |
| 4,651,716 A | 3/1987 | Forester et al. ............. 128/1 D |
| 4,674,518 A | 6/1987 | Salo ........................... 128/695 |
| 4,686,987 A | 8/1987 | Salo et al. ............. 128/419 PG |
| 4,693,253 A | 9/1987 | Adams ..................... 128/419 D |
| 4,871,351 A | 10/1989 | Feingold ..................... 604/66 |
| 4,880,005 A | 11/1989 | Pless et al. ............. 128/419 PG |
| 4,897,987 A | 2/1990 | Spalla ........................ 56/16.7 |
| 4,904,472 A | 2/1990 | Belardinelli et al. ........ 514/263 |
| 4,924,875 A | 5/1990 | Chamoun ................... 600/509 |
| 4,944,299 A | 7/1990 | Silvian ................. 128/419 PG |
| 4,980,379 A | 12/1990 | Belardinelli et al. ........ 514/821 |
| 4,987,897 A | 1/1991 | Funke .................. 128/419 PG |
| 5,002,052 A | 3/1991 | Haluska ............... 128/419 PG |
| 5,014,698 A | 5/1991 | Cohen ....................... 128/419 |

(Continued)

FOREIGN PATENT DOCUMENTS

EP 0054138 10/1981

(Continued)

OTHER PUBLICATIONS

Rosborough, John.P. ,et al. ,"Electrical Therapy for Pulseless Electrical Activity", NASPE, Apr. 2000, v. 23, Part II., Abstract,(2000), 591.

(Continued)

*Primary Examiner*—Jeffrey R. Jastrzab
*Assistant Examiner*—John D Alexander
(74) *Attorney, Agent, or Firm*—Schwegman, Lundberg, Woessner & Kluth, P.A.

(57) ABSTRACT

An apparatus and method is presented for improving cardiac function after successful termination of a tachyarrhythmia such as ventricular fibrillation. A series of electrical stimulation pulses are delivered prior to a defibrillation shock if one or more specific criteria are met.

12 Claims, 5 Drawing Sheets

U.S. PATENT DOCUMENTS

| | | | |
|---|---|---|---|
| 5,040,533 A | 8/1991 | Fearnot | 128/419 PG |
| 5,041,107 A | 8/1991 | Heil, Jr. | 604/891.1 |
| 5,042,497 A | 8/1991 | Shapland | 600/509 |
| 5,058,581 A | 10/1991 | Silvian | 128/419 PG |
| 5,087,243 A | 2/1992 | Avitall | 604/20 |
| 5,113,869 A | 5/1992 | Nappholz et al. | |
| 5,127,404 A | 7/1992 | Wyborny et al. | 128/419 P |
| 5,137,019 A | 8/1992 | Pederson et al. | 128/419 |
| 5,190,035 A | 3/1993 | Salo et al. | 128/419 |
| 5,215,083 A | 6/1993 | Drane et al. | 128/419 D |
| 5,220,917 A | 6/1993 | Cammilli et al. | 128/419 D |
| 5,269,301 A | 12/1993 | Cohen | 607/6 |
| 5,282,836 A | 2/1994 | Kreyenhagen et al. | 607/4 |
| 5,284,136 A | 2/1994 | Hauck et al. | 607/24 |
| 5,305,745 A | 4/1994 | Zacouto | 128/637 |
| 5,330,505 A * | 7/1994 | Cohen | 607/6 |
| 5,334,222 A | 8/1994 | Salo et al. | 607/17 |
| 5,342,408 A | 8/1994 | deCoriolis et al. | 607/32 |
| 5,353,800 A | 10/1994 | Pohndorf et al. | 128/673 |
| 5,354,317 A | 10/1994 | Alt | 607/19 |
| 5,366,485 A | 11/1994 | Kroll et al. | 607/5 |
| 5,368,028 A | 11/1994 | Palti | 128/635 |
| 5,391,190 A | 2/1995 | Pederson et al. | 607/23 |
| 5,404,877 A | 4/1995 | Nolan et al. | 128/671 |
| 5,405,362 A | 4/1995 | Kramer et al. | 607/5 |
| 5,416,695 A | 5/1995 | Stutman et al. | 364/413.02 |
| 5,417,717 A | 5/1995 | Salo et al. | 607/18 |
| 5,431,682 A | 7/1995 | Hedberg | 607/5 |
| 5,441,525 A | 8/1995 | Shelton et al. | 607/23 |
| 5,456,692 A | 10/1995 | Smith, Jr. et al. | 607/31 |
| 5,460,605 A | 10/1995 | Tuttle et al. | 604/67 |
| 5,464,434 A | 11/1995 | Alt | 607/6 |
| 5,487,752 A | 1/1996 | Salo et al. | 607/17 |
| 5,496,360 A | 3/1996 | Hoffmann et al. | 607/120 |
| 5,499,971 A | 3/1996 | Shapland et al. | 604/53 |
| 5,501,701 A | 3/1996 | Markowitz et al. | 607/9 |
| 5,540,728 A | 7/1996 | Shelton et al. | 607/23 |
| 5,551,953 A | 9/1996 | Lattin et al. | 604/20 |
| 5,556,421 A | 9/1996 | Prutchi et al. | 607/36 |
| 5,562,711 A | 10/1996 | Yerich et al. | 607/17 |
| 5,562,713 A | 10/1996 | Silvian | 607/32 |
| 5,579,876 A | 12/1996 | Adrian et al. | 188/322.17 |
| 5,584,868 A | 12/1996 | Salo et al. | 607/17 |
| 5,586,556 A | 12/1996 | Spivey et al. | 128/697 |
| 5,603,331 A | 2/1997 | Heemels et al. | 128/696 |
| 5,607,418 A | 3/1997 | Arzbaecher | 604/891.1 |
| 5,607,463 A | 3/1997 | Schwartz et al. | 623/1.44 |
| 5,634,899 A | 6/1997 | Shapland et al. | 604/51 |
| 5,662,689 A | 9/1997 | Elsberry et al. | 607/5 |
| 5,676,686 A | 10/1997 | Jensen et al. | 607/9 |
| 5,690,682 A | 11/1997 | Buscemi et al. | 607/3 |
| 5,690,683 A * | 11/1997 | Haefner et al. | 607/4 |
| 5,693,075 A | 12/1997 | Plicchi et al. | 607/17 |
| 5,703,125 A | 12/1997 | Bovy et al. | 128/637 |
| 5,706,829 A | 1/1998 | Kadri | 128/898 |
| 5,720,770 A | 2/1998 | Nappholz et al. | 607/30 |
| 5,725,561 A | 3/1998 | Stroebel et al. | 607/9 |
| 5,725,562 A | 3/1998 | Sheldon | 607/19 |
| 5,730,125 A | 3/1998 | Prutchi et al. | 128/637 |
| 5,749,900 A | 5/1998 | Schroeppel et al. | 607/4 |
| 5,782,879 A | 7/1998 | Rosborough et al. | 607/6 |
| 5,800,464 A | 9/1998 | Kieval | 607/9 |
| 5,800,498 A | 9/1998 | Obino et al. | 607/123 |
| 5,814,089 A | 9/1998 | Stokes et al. | 607/32 |
| 5,817,131 A | 10/1998 | Elsberry et al. | 607/5 |
| 5,833,603 A | 11/1998 | Kovacs et al. | 600/317 |
| 5,836,935 A | 11/1998 | Ashton et al. | 604/891.1 |
| 5,851,220 A * | 12/1998 | Murphy | 607/5 |
| 5,874,420 A | 2/1999 | Pelleg | 514/81 |
| 5,876,353 A | 3/1999 | Riff | 600/547 |
| 5,893,881 A | 4/1999 | Elsberry et al. | 607/5 |
| 5,899,928 A | 5/1999 | Sholder et al. | 607/27 |
| 5,913,879 A | 6/1999 | Ferek-Petric et al. | 607/14 |
| 5,919,210 A | 7/1999 | Lurie et al. | 607/3 |
| 5,925,066 A | 7/1999 | Kroll et al. | 607/3 |
| 5,949,659 A | 9/1999 | Lesche | 363/16 |
| 5,954,761 A | 9/1999 | Macheck et al. | 607/126 |
| 5,957,861 A | 9/1999 | Combs et al. | 600/547 |
| 5,957,957 A | 9/1999 | Sheldon | 607/17 |
| 5,967,986 A | 10/1999 | Cimochowski et al. | 600/454 |
| 5,978,705 A | 11/1999 | KenKnight et al. | 607/5 |
| 5,991,668 A | 11/1999 | Leinders et al. | 607/125 |
| 6,016,443 A | 1/2000 | Ekwall et al. | |
| 6,016,447 A | 1/2000 | Juran et al. | 607/27 |
| 6,016,448 A | 1/2000 | Busacker et al. | 607/29 |
| 6,022,322 A | 2/2000 | Prutchi | 600/506 |
| 6,035,233 A | 3/2000 | Schroeppel et al. | 600/515 |
| 6,044,297 A | 3/2000 | Sheldon et al. | 607/17 |
| 6,049,735 A | 4/2000 | Hartley et al. | 607/9 |
| 6,070,590 A * | 6/2000 | Hoffmann | 128/898 |
| 6,076,015 A | 6/2000 | Hartley et al. | 607/20 |
| 6,078,834 A | 6/2000 | Lurie et al. | 607/3 |
| 6,104,949 A | 8/2000 | Pitts Crick et al. | 600/547 |
| 6,112,116 A | 8/2000 | Fischell et al. | |
| 6,115,636 A | 9/2000 | Ryan | 607/60 |
| 6,128,526 A | 10/2000 | Stadler et al. | 600/517 |
| 6,140,740 A | 10/2000 | Porat et al. | 310/322 |
| 6,141,588 A | 10/2000 | Cox et al. | 607/9 |
| 6,154,672 A | 11/2000 | Pendekanti et al. | 607/5 |
| 6,154,675 A | 11/2000 | Juran et al. | 607/29 |
| 6,155,267 A | 12/2000 | Nelson | 128/899 |
| 6,161,042 A | 12/2000 | Hartley et al. | 607/20 |
| 6,168,801 B1 | 1/2001 | Heil, Jr. et al. | 424/426 |
| 6,198,394 B1 | 3/2001 | Jacobsen et al. | 340/573.1 |
| 6,200,265 B1 | 3/2001 | Walsh et al. | 600/300 |
| 6,203,495 B1 | 3/2001 | Bardy | 600/301 |
| 6,206,914 B1 | 3/2001 | Soykan et al. | 623/1.42 |
| 6,213,942 B1 | 4/2001 | Flach et al. | 600/300 |
| 6,221,011 B1 | 4/2001 | Bardy | 600/300 |
| 6,231,516 B1 | 5/2001 | Keilman et al. | 600/485 |
| 6,237,398 B1 | 5/2001 | Porat et al. | 73/54.09 |
| 6,253,108 B1 | 6/2001 | Rosborough et al. | 607/14 |
| 6,254,573 B1 | 7/2001 | Haim et al. | 604/157 |
| 6,256,233 B1 | 7/2001 | Glass | 365/189.05 |
| 6,259,949 B1 | 7/2001 | Rosborough et al. | 607/14 |
| 6,261,230 B1 | 7/2001 | Bardy | 600/300 |
| 6,263,241 B1 | 7/2001 | Rosborough et al. | 607/6 |
| 6,264,606 B1 | 7/2001 | Ekwall et al. | |
| 6,266,563 B1 * | 7/2001 | KenKnight et al. | 607/5 |
| 6,270,457 B1 | 8/2001 | Bardy | 600/300 |
| 6,272,377 B1 | 8/2001 | Sweeney et al. | |
| 6,273,377 B1 | 8/2001 | Sweeney et al. | 600/515 |
| 6,277,072 B1 | 8/2001 | Bardy | 600/300 |
| 6,277,078 B1 | 8/2001 | Porat et al. | 600/486 |
| 6,278,894 B1 | 8/2001 | Salo et al. | 600/547 |
| 6,280,380 B1 | 8/2001 | Bardy | 600/300 |
| 6,285,898 B1 | 9/2001 | Ben-Haim | 600/374 |
| 6,298,267 B1 | 10/2001 | Rosborough et al. | 607/6 |
| 6,298,272 B1 | 10/2001 | Peterfeso et al. | 607/120 |
| 6,309,370 B1 | 10/2001 | Haim et al. | 604/66 |
| 6,312,378 B1 | 11/2001 | Bardy | 600/300 |
| 6,317,615 B1 | 11/2001 | KenKnight et al. | 600/372 |
| 6,317,631 B1 | 11/2001 | Ben-Haim et al. | 607/9 |
| 6,331,160 B1 | 12/2001 | Bardy | 600/300 |
| 6,336,903 B1 | 1/2002 | Bardy | 600/508 |
| 6,358,202 B1 | 3/2002 | Arent | 600/300 |
| 6,358,203 B1 | 3/2002 | Bardy | 600/300 |
| 6,361,522 B1 | 3/2002 | Scheiner et al. | 604/67 |
| 6,361,780 B1 | 3/2002 | Ley et al. | 424/400 |
| 6,368,284 B1 | 4/2002 | Bardy | 600/508 |
| 6,370,424 B1 | 4/2002 | Prutchi | 600/547 |
| 6,398,728 B1 | 6/2002 | Bardy | 600/300 |
| 6,411,840 B1 | 6/2002 | Bardy | 600/513 |
| 6,411,844 B1 | 6/2002 | Kroll et al. | 607/5 |

| | | | |
|---|---|---|---|
| 6,424,847 B1 | 7/2002 | Mastrototaro et al. | 600/316 |
| 6,440,066 B1 | 8/2002 | Bardy | 600/300 |
| 6,442,413 B1 | 8/2002 | Silver | 600/345 |
| 6,443,949 B1 | 9/2002 | Altman | 606/41 |
| 6,453,195 B1 | 9/2002 | Thompson | 607/3 |
| 6,459,917 B1 | 10/2002 | Gowda et al. | 600/345 |
| 6,459,929 B1 | 10/2002 | Hopper et al. | 600/513 |
| 6,468,263 B1 | 10/2002 | Fischell et al. | 604/890.1 |
| 6,473,640 B1 | 10/2002 | Erlebacher | 600/547 |
| 6,478,737 B1 | 11/2002 | Bardy | 600/301 |
| 6,501,983 B1 | 12/2002 | Natarajan et al. | 600/517 |
| 6,511,477 B1 | 1/2003 | Altman et al. | 606/41 |
| 6,518,245 B1 | 2/2003 | Anderson et al. | 514/14 |
| 6,519,488 B1 | 2/2003 | KenKnight et al. | 600/372 |
| 6,556,865 B1 | 4/2003 | Walcott et al. | 607/6 |
| 6,689,117 B1 | 2/2004 | Sweeney et al. | 604/503 |
| 6,760,621 B1 | 7/2004 | Walcott et al. | 607/6 |
| 6,813,516 B1 * | 11/2004 | Ujhelyi et al. | 607/4 |
| 6,892,094 B1 * | 5/2005 | Ousdigian et al. | 607/4 |
| 2001/0000802 A1 | 5/2001 | Soykan et al. | 623/1.13 |
| 2002/0026228 A1 | 2/2002 | Schauerte | 607/122 |
| 2002/0099328 A1 | 7/2002 | Scheiner et al. | |
| 2003/0004403 A1 | 1/2003 | Drinan et al. | 600/301 |
| 2003/0045805 A1 | 3/2003 | Sheldon et al. | |
| 2003/0060854 A1 | 3/2003 | Zhu | 607/25 |
| 2003/0069606 A1 | 4/2003 | Girouard et al. | 607/3 |
| 2003/0153952 A1 | 8/2003 | Auricchio et al. | 607/9 |
| 2003/0158584 A1 | 8/2003 | Cates et al. | 607/2 |
| 2003/0208240 A1 | 11/2003 | Pastore et al. | 607/17 |
| 2003/0233132 A1 | 12/2003 | Pastore et al. | 607/17 |
| 2004/0002739 A1 | 1/2004 | Cates et al. | 607/6 |
| 2004/0093034 A1 | 5/2004 | Girouard et al. | 607/3 |

FOREIGN PATENT DOCUMENTS

| | | |
|---|---|---|
| EP | 0467695 A2 | 1/1992 |
| EP | 0545628 A2 | 6/1993 |
| EP | 0620420 | 10/1994 |
| EP | 1050265 | 11/2000 |
| WO | WO-97/25098 A1 | 7/1997 |
| WO | WO-97/33513 | 9/1997 |
| WO | WO-98/34537 A1 | 8/1998 |
| WO | WO-00/04947 A2 | 2/2000 |
| WO | WO-00/07497 A1 | 2/2000 |
| WO | WO-01/08748 A1 | 2/2001 |
| WO | WO-01/30436 A2 | 5/2001 |

OTHER PUBLICATIONS

Arnaud, Claire, et al., "iNOS is a mediator of the heat stress-induced preconditioning against myocardial infarction in vivo in the rat", *Cardiovascular Research*, 58, (2003),118-125.

Brunner, Friedrich, et al., "Attenuation of myocardial ischemia/reperfusion injury in mice with myocyte-specific overexpression of endothelial nitric oxide synthase", *Cardiovascular Research*, 57, (2003),55-62.

Ferdinandy, Peter, et al., "Nitric oxide, superoxide, and peroxynitrite in myocardial ischaemia-reperfusion injury and preconditioning", *British Journal of Pharmacology*, vol. 138, No. 4, (2003),532-543.

Flogel, Ulrich, et al., "Myoglobin: A scanvenger of bioactive NO", *PNAS*, vol. 98, No. 2, (Jan. 16, 2001),735-740.

Gewaltig, Michael T., et al., "Vasoprotection my nitric oxide: mechanisms and therapeutic potential", *Cardiovascular Research*, 55, (Feb. 14, 2002),250-260.

Hada, Yoshiyuki, et al., "Pulsus alternans determined by biventricular simultaneous systolic time intervals", *Circulation*, vol. 65, No. 3, (Mar. 1982),617-26.

Konta, Tsuyoshi, et al., "Significance of Discordant ST Alternans in Ventricular Fibrillation", *Circulation*, vol. 82, No. 6, Dec. 1990, American Heart Association,(1990),2185-2189.

Lee, Y. C., et al., "Pulsus alternans in patients with congestive cardiomyopathy", *Circulation*, vol. 65, No. 7. (Jun. 1982),1533-4.

Li, Qianghong, et al., "Gene Therapy With Inducible Nitric Oxide Synthase Protects Against Myocardial Infarction via a Cyclooxygenase-2-Dependent Mechanism", *Circulation Research*, 92, (2003),741-748.

Lovett, Eric G., "Technique for Discriminating Between Coordinated and Uncoordinated Cardiac Rhythms", U.S. Appl. No. 10/435,487, filed May, 9, 2003, assigned to Cardiac Pacemakers, Inc., 36 pgs.

Luepker, R. V., et al., "Transthoracic Electrical Impedance: Quantitative Evaluation of a Non-Invasive Measure of Thoracic Fluid Volume", *American Heart Journal*, vol. 85, No. 1,(Jan. 1973),83-93.

Mai, J., et al., "Enhanced Rate Response Algorithm for Orthostatic Compensation Pacing", *Pace*, 23, Naspe Abstracts, Abstract No. 678,(Apr. 2000),p. 722.

Min, Mart, et al., "Electrical Impedance and Cardiac Monitoring-Technology, Potential and Applications", *International Journal of Bioelectromagnetism*, 5, (2003).53-56.

Ostadal, Petr, et al., "The effect of early treatment by cerivastatin on the serum level of C-reactive protein, interleukin-6, and interleukin-8 in patients with unstable angina and non-Q-wave myocardial infarction", *Molecular and Cellular Biochemistry*, 246, (2003),45-50.

Paolocci, Nazareno, et al., "Positive inotropic and lusitropic effects of HNO/NO- in falling hearts: Independence from beta-adrenergic signaling", *PNAS*, vol. 100, No. 9, (Apr. 29, 2003),5537-5542.

Pastore, Joseph M., et al., "Method And Apparatus For Modulating Cellular Metabolism During Post-Ischemia Or Heart Failure", U.S. Appl. No. 10/645,823, filed Aug. 21, 1003, 46 pages.

Rubenstein, Donald S., et al., "Premature Beats Elicit a Phase Reversal of Mechanoelectrical Alternans in Cat Ventricular Myocytes", *Circulation*, vol. 91, No. 1, Jan. 1995, American Heart Association,(Jan. 1, 1995),201-214.

Salloum, Fadi, et al., "Sildenafil Induces Delayed Preconditioning Through Inducible Nitric Oxide Synthase-Dependent Pathway in Mouse Heart", *Circulation Research*, 92, (Apr. 4, 2003),595-597.

Schaefer, Saul, et al., "Clinical and hemodynamic characteristics of patients with inducible pulsus alternans", *American Heart Journal*, vol. 115, No. 6, (Jun. 1988),1251-7.

Smith, Damon, et al., "Influence of the Aortic Component of the Second Heart Sound on Left Ventricular Maximal Negative dP/dt in the Dog", *Am. J. Cardiol.*, 55: 205, (1985),205-209.

Suematsu, Yoshihiro, et al., "L-Arginine given after ischaemic preconditioning can enhance cardioprotection in isolated rat hearts", *European Journal of Cardio-thoracic Surgery*, 19, (2001),873-879.

Woldbaek, Per R., et al., "Increased cardiac IL-18 mRNA, pro-IL-18 and plasma IL-18 after myocardial infarction in the mouse; a potential role in cardiac dysfunction", *Cardiovascular Research*, 59, (2003),122-131.

Wolfrum, Sebastian, et al., "Acute Reduction of Myocardial Infarct Size By a Hydroxymethyl Glutaryl Coenzyme A Reductase Inhibitor Is Mediated By Endothelial Nitric Oxide Synthase", *J. Cardiovas Pharmacol*, vol. 41, No. 3, (Mar. 2003),474-480.

Wunderlich, Carsten, et al., "Acute Inhibition of Myoglobin Impairs Contractility and Energy State of iNOS-Overexpressing Hearts", *Circulation Research*, 92, (2003),1352-1358.

Bralet, J, et al., "Vasopeptidase inhibitors: an emerging class of cardiovascular drugs", *Trends Pharmacol Sci.*, 22(3), (Mar. 2001),106-9.

Burns, Brent E., "Fabrication Technology for a Chronic In-Vivo Pressure Sensor", *1984 International Electron Devices Meeting Technical Digest*, (1984),210-212.

Carr, William N., et al., "Integrated Pressure Sensor With Remote Power Source and Remote Readout", *The 8th International Conference on Solid-State Sensors and Actuators and Eurosensors IX*, Digest of Technical Papers, Stockholm, Sweden, (Jun. 25-29, 1995),624-627.

Chau, Hin-Leung, et al., "An Ultraminiature Solid-State Pressure Sensor for a Cardiovascular Catheter", *IEEE Transactions on Electron Devices*, (Dec. 1988),2355-2362.

Colonna, P, "Myocardial infarction and left ventricular remodeling: results of the CEDIM trial. Carnitine Ecocardiografia Digitalizzata Infarto Miocardico.", *Am Heart J.*, (Feb. 2000, 139(2 Pt 3)),S124-30.

Lehman, J, et al., "Gene regulatory mechanisms governing energy metabolism during cardiac hypertrophic growth", *Heart Fail Rev.*, (Apr. 2000),175-85.

Levin, L, "Researchers present findings at European cardiology conference", Advisory Board Daily Briefing, 8, Clinical Outlook, (Sep. 2002),8 pages [see pgs. 5,6].

Lopaschuk, G, "Metabolic abnormalities in the diabetic heart", *Heart Fail Rev.*, (Apr. 2002),149-59.

Luepker, R., "Transthoracic Electrical Impedance: Quantitative Evaluation of a Non-Invasive Measure of Thoracic Fluid Volume", *American Heart Journal*, 85(1), (Jan. 1973),83-93.

Mai, J., "Enhanced Rate Response Algorithm for Orthostatic Compensation Pacing", *Pacing Clin Electrophysiol.* (PACE) Abstracts, 23 (Pt 2), (Apr. 2000),722.

Paolocci, Nazareno, et al., "Positive inotropic and lusitropic effects of HNO/NO- in failing hearts: independence from beta-adrenergic signaling", *Proceedings of the National Academy of Sciences USA*, 100(9), (Apr. 29, 2003),4978-80.

Pastore, Joseph M., et al., "Drug Delivery System and Method Employing External Drug Delivery Device in Conjunction With Computer Network", U.S. Appl. No. 10/742,574, filed Dec. 19, 2003, 36 pages.

Rizos, I, "Three-year survival of patients with heart failure caused by dilated cardiomyopathy and L-carnitine administration", *Am Heart J.*, 139(2 Pt 3), (Feb. 2000),Am Heart J.

Sabbah, H, et al., "Partial fatty acid oxidation inhibitors: a potentially new class of drugs for heart failure", *Eur J Heart Fail.*, 4(1), (Jan. 2002),3-6.

Spiegel, Egbert, "A CMOS Sensor and Signal Conversion Chip for Monitoring Arterial Blood Pressure and Temperature", *IEEE International Solid-State Circuits Conference.*, (Feb. 20, 1992),126-127.

Stanley, W, et al., "Energy metabolism in the normal and failing heart: potential for therapeutic interventions", *Heart Fail Rev.*, (Apr. 2002),115-30.

Stanley, W, "Partial fatty acid oxidation inhibitors for stable angina", *Expert Opin Investig Drugs*, 11(5), (May 2002),615-29.

Wolff, A, et al., "Metabolic approaches to the treatment of ischemic heart disease: the clinicians' perspective", *Heart Fail Rev.*, (Apr. 2002),187-203.

Wynn, R, "Cardiovascular drugs and dental considerations", *Cardiovascular drugs and dental considerations*. J. Calif Dent Assoc., 28(7), (Jul. 2000),9-26.

Ziaie, Babak, et al., "A Single-Channel Implantable Microstimulator for Functional Neuromuscular Stimulation", *IEEE Transactions of Biomedical Engineering*, 44, (Oct. 1997),909-920.

* cited by examiner

METHOD AND APPARATUS FOR DELIVERING PRE-SHOCK DEFIBRILLATION THERAPY

FIELD OF THE INVENTION

This invention pertains to apparatus and methods for treating cardiac arrhythmias and improving cardiac function.

BACKGROUND

Tachyarrhythmias are abnormal heart rhythms characterized by a rapid heart rate. Examples of ventricular tachyarrhythmias include ventricular tachycardia (VT) and ventricular fibrillation (VF). Both ventricular tachycardia and ventricular fibrillation can be hemodynamically compromising, and both can be life-threatening. Ventricular fibrillation, however, causes circulatory arrest within seconds and is the most common cause of sudden cardiac death. Cardioversion (an electrical shock delivered to the heart synchronously with an intrinsic depolarization) and defibrillation (an electrical shock delivered without such synchronization) can be used to terminate most tachyarrhythmias, including VT and VF. As used herein, the term defibrillation and cardioversion should be taken to mean an electrical shock delivered either synchronously or not in order to terminate a fibrillation. In electrical defibrillation, a current depolarizes a critical mass of myocardial cells so that the remaining myocardial cells are not sufficient to sustain the fibrillation.

Implantable cardioverter/defibrillators (ICDs) provide electro-therapy by delivering a shock pulse to the heart when fibrillation is detected by the device. The ICD is a computerized device containing a pulse generator that is usually implanted into the chest or abdominal wall. Electrodes connected by leads to the ICD are placed on the heart, or passed transvenously into the heart, to sense cardiac activity and to conduct the impulses from the shock pulse generator. The device delivers a defibrillation shock pulse to the heart in response to a detected tachyarrhythmia by impressing a voltage between shock electrodes in contact with the heart.

SUMMARY OF THE INVENTION

The present invention relates to an apparatus and method for preventing post-shock hypotension after termination of ventricular fibrillation. The invention may be incorporated in an ICD or an external defibrillation device. Post-shock cardiac function is improved by delivering a series of electrical stimulation pulses prior to a defibrillation shock while the heart is in fibrillation. In order to avoid delaying an initial defibrillation shock, such pre-shock stimulation therapy is only applied after one or more failed defibrillation attempts, according to the duration of the tachyarrhythmia, or according to the energy level of the defibrillation shock.

DETAILED DESCRIPTION

It has been found that transient hypotension often occurs following defibrillation shocks. This hypotension may last for seconds, minutes, or even hours and can result in post-shock fatigue in some patients. Some evidence suggests that the likelihood of post-shock hypotension is related to the duration of the fibrillation, and that arterial pressure will quickly return to normal if successful cardioversion occurs within approximately thirty seconds in most patients. Patients who remain in VF for a longer period of time, especially after repeated defibrillation attempts, are more likely to experience transient hypotension after successful cardioversion.

In order to improve post-shock cardiac function, and in some cases increase the likelihood of successful cardioversion, a series of electrical stimulation pulses can be delivered prior to the defibrillation shock. By way of example but not by way of limitation, such pulses may be delivered as a pulse train at a frequency range between 10 and 100 Hz, at an amplitude between 15 and 200 volts, and for a duration of between 100 milliseconds and 2 seconds. Delivering such stimulation pulses while the heart is in fibrillation allows the pulses to be delivered without regard to the intrinsic heart rhythm. Since a patient in VF is in circulatory arrest, however, it is normally considered desirable to delivery defibrillation therapy as soon as possible. In accordance with the present invention, therefore, a series of stimulation pulses are delivered during VF and before a defibrillation shock only after an initial defibrillation shock has failed to cardiovert the patient. In other embodiments, decision algorithms may use additional criteria before delivering pre-shock stimulation therapy such as the duration of the VF, the number of failed defibrillation attempts, and the energy level of defibrillation shock in cases where shocks of increasing magnitude are delivered. By invoking pre-shock stimulation therapy in only these situations, no delay of initial therapy occurs, and the therapy is applied only when it is needed most.

1. Hardware Platform

Figure 1:
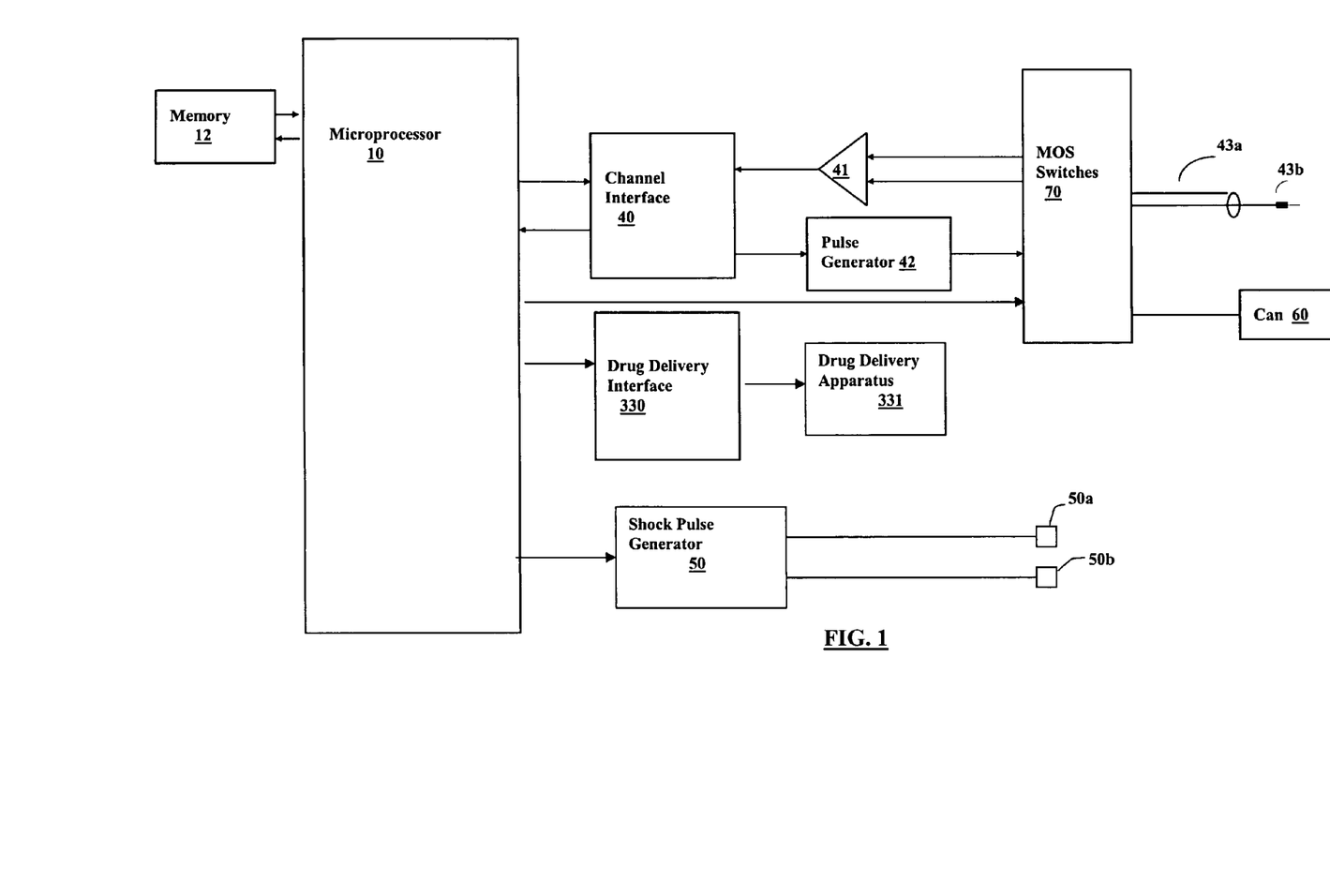
FIG. 1 is a system diagram of an exemplary cardiac rhythm management device in which may be incorporated the present invention.

The present invention may be incorporated into either an external defibrillator or an ICD. The description that follows, however, will principally refer to an ICD configured and programmed to carry out the method of delivering pre-shock stimulation therapy described above. Cardiac rhythm management devices such as ICDs are typically implanted subcutaneously on a patient's chest and have leads threaded intravenously into the heart to connect the device to electrodes used for sensing and delivery of defibrillation shocks. A programmable electronic controller causes defibrillation shocks to be delivered when an arrhythmia is detected. The controller also controls the output of pacing pulses in the case of an ICD with pacemaker functionality. The present invention may be incorporated into an ICD or incorporated into an external defibrillation device. For illustrative purposes, however, a block diagram of an implantable device with cardioversion/defibrillation capability is shown in FIG. 1. The controller of the device is made up of a microprocessor 10 communicating with a memory 12, where the memory 12 may comprise a ROM (readonly memory) for program storage and a RAM (random-access memory) for data storage. The controller could be implemented by other types of logic circuitry (e.g., discrete components or programmable logic arrays) using a state machine type of design, but a microprocessor-based system is preferable.

The device has a sensing channel for sensing cardiac electrical activity and a stimulation channel for delivering stimulation pulses. The device would normally be implanted such that the ventricles are sensed and stimulated by the respective channels. Each channel in this embodiment utilizes a single lead connected to the device that includes a ring electrode 43a and tip electrode 43b for bipolar sensing and stimulation. In certain embodiments, the device may incorporate a pacemaker functionality in which case the stimulation channel may also be used for delivering paces to the heart in accordance with a pacing algorithm. A MOS switching network 70 controlled by the microprocessor is used to switch the electrodes to the input of a sense amplifier 41 for the sensing channel or to the output of a pulse generator 42 for the stimulation channel. The switching network may also be used to connect only one of either the ring or tip electrode to the pulse generator 42 or sensing amplifier 41 for unipolar sensing or stimulation, in which case the conductive case of the device or can 60 is used as the other electrode. A channel interface 40 which communicates bidirectionally with a port of microprocessor 10 may include an analog-to-digital converter for digitizing sensing signal inputs from the sensing amplifier, registers that can be written to for adjusting the gain and threshold values of the sensing amplifier, and registers for controlling the output of stimulation pulses and/or changing the stimulation pulse amplitude or frequency. A defibrillation shock pulse generator 50 with shock leads 50a and 50b for delivering cardioversion/defibrillation shocks to the ventricles is also interfaced to the controller. In an alternative embodiment, the stimulation channel may use the shock leads rather than the sensing lead for delivering stimulation pulses.

The microprocessor 10 controls the overall operation of the device in accordance with programmed instructions stored in memory. The sensing channel detects a chamber sense, either an atrial sense or ventricular sense, when an electrogram signal (i.e., a voltage sensed by an electrode representing cardiac electrical activity) generated by the channel exceeds a specified detection threshold. The time intervals between such senses are measured in order to detect tachyarrhythmias so that appropriate therapy can be delivered by the device. Upon detection of a tachyarrhythmia warranting intervention (e.g., ventricular fibrillation), the controller causes the delivery of a shock pulse to the heart. As described below with reference to different embodiments, the controller is also programmed to deliver pre-shock stimulation pulses via the stimulation channel when certain criteria are met.

2. Exemplary Decision Algorithms

Figure 2A:
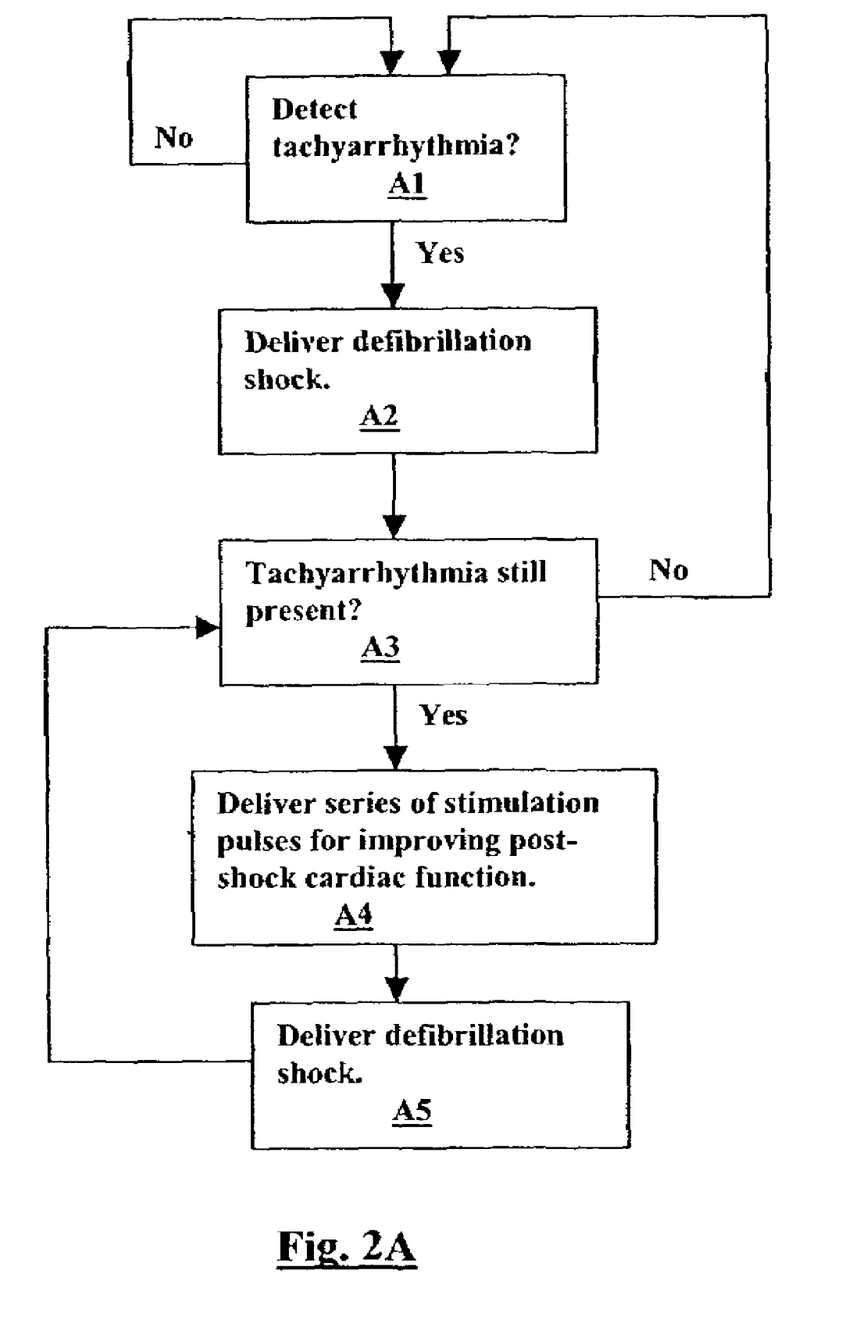
FIGS. 2A through 2D illustrate exemplary algorithms for delivering stimulation pulses to improve cardiac function.

FIGS. 2A through 2D illustrate decision algorithms for delivering pre-shock stimulation therapy as could be implemented in the programming of the device in FIG. 1. Referring first to FIG. 2A, the cardiac rhythm is monitored at step A1 by detecting ventricular senses (R waves) and determining if a ventricular tachyarrhythmia such as VF exists. If a ventricular tachyarrhythmia has been detected, a defibrillation shock is delivered at step A2. This defibrillation shock is delivered without delay and not preceded by stimulation pulses. At step A3, it is determined whether the tachyarrhythmia is still present. If the patient has been successfully cardioverted, the device returns to step A1. If the tachyarrhythmia is still present, a series of stimulation pulses at a specified frequency, magnitude, and duration is delivered at step A4 before the next defibrillation shock is delivered at step A5. The device then returns to step A3 to see if the defibrillation shock was successful. Thus, in this embodiment, pre-shock stimulation therapy for improving cardiac function is delivered prior to each defibrillation shock only after an initial failure of a defibrillation shock delivered immediately after detection of the tachyarrhythmia.

Figure 2B:
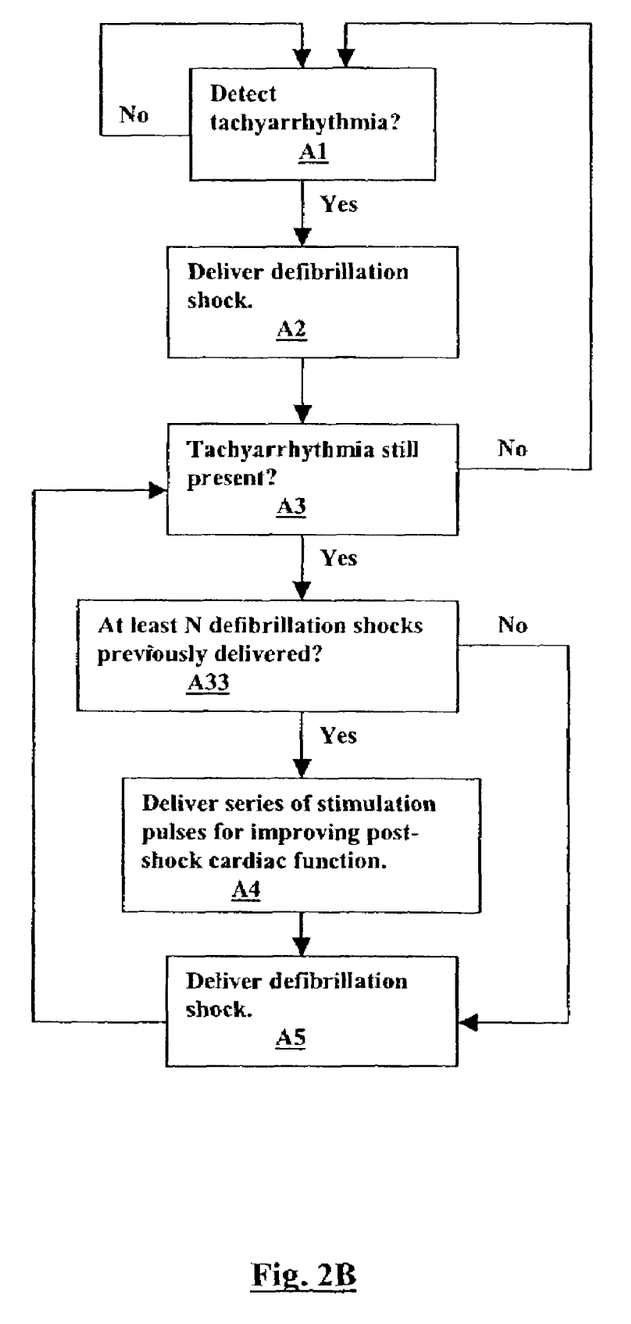
Figure 2C:
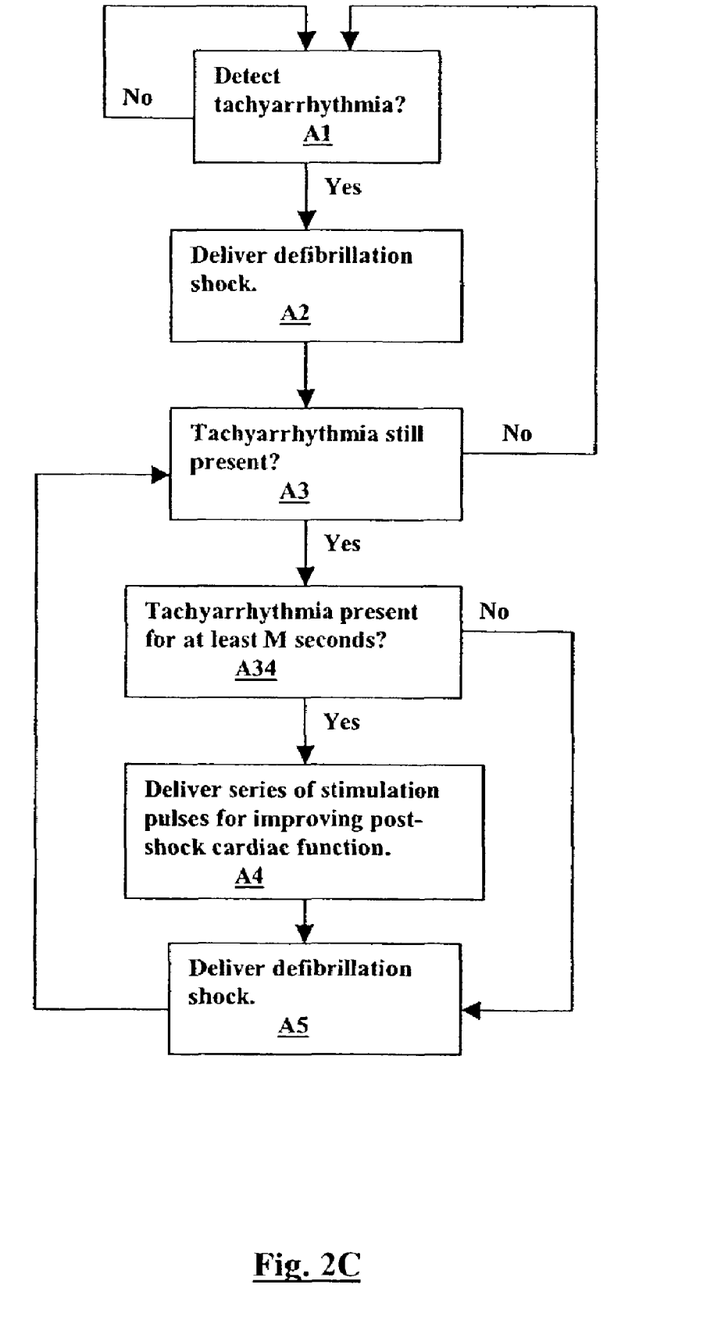

FIG. 2B shows an alternative embodiment in which an additional step A33 is performed after it is determined that a tachyarrhythmia is still present at step A3. Step A33 adds the requirement that at least N previous unsuccessful defibrillation shocks must have been applied before pre-shock stimulation therapy is delivered at step A4. FIG. 2C shows another embodiment in which step A34 is added after step A3 in order to test the duration of the tachyarrhythmia. In this case, pre-shock stimulation therapy is delivered at step A4 only if it is determined that the tachyarrhythmia has been present for at least M seconds.

Figure 2D:
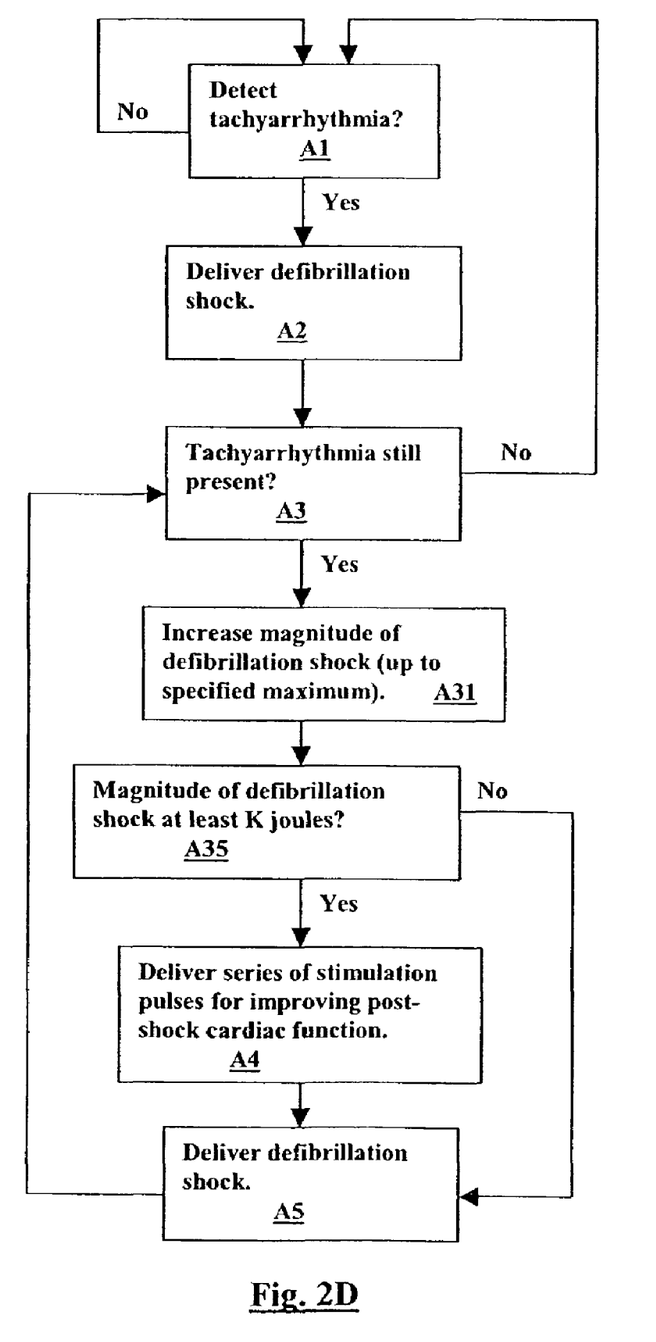

FIG. 2D shows an embodiment in which pre-shock stimulation therapy is applied or not in accordance with the energy level of the defibrillation shock. Ventricular fibrillation is a phenomena that exhibits a threshold with respect to the shock magnitude and duration needed to terminate the fibrillation by changing the transmembrane potential in a critical mass of myocardial cells. The ventricular defibrillation threshold (VDFT), for example, is defined the smallest amount of energy that can be delivered to the heart to reliably convert ventricular fibrillation to normal sinus rhythm. The larger the magnitude of the shocks delivered by an ICD, the more the battery is drained, thus decreasing the longevity of the device, and the more discomfort is inflicted upon the patient. It is desirable, therefore, for defibrillation shocks to be as small and close to the VDFT as possible. When a defibrillation shock is unsuccessful in terminating a tachyarrhythmia, however, an ICD may be programmed to increase the energy of the defibrillation shock. The magnitude of the defibrillation shock may be increased after each successive failed shock or after a specified number of failed shocks to implement a kind of tiered therapy with respect to shocking energy level. The embodiment of FIG. 2D adds step A31 to increase the energy level of the defibrillation shock up to a specified maximum after each failed defibrillation attempt. Step A35 then determines if the energy level of the defibrillation shock is at least K joules before pre-shock stimulation therapy is delivered at step A34.

In an alternative embodiment, once the controller 10 detects a tachyarrhythmia warranting intervention, a command may also be issued to the drug delivery interface 330. The drug delivery interface then actuates a drug delivery apparatus 331 incorporated into the device that delivers a quantity of a pharmacological or neurohumoral agent for improving post-shock cardiac function. (e.g., epinephrine or norepinephrine). The drug delivery apparatus may take a number of forms. One example of such an apparatus is a pump and a drug reservoir located within a header portion of the device, where the pump communicates with an intravenously disposed catheter. The drug delivery interface within the housing communicates with the pump by control wires that pass into the header through a feedthrough. Upon actuation by the drug delivery interface 330, the pump pumps a quantity of drug from a reservoir into the lumen of the catheter.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A cardiac rhythm management device, comprising:
   a sensing channel for generating electrograms reflecting cardiac electrical activity;
   a defibrillation shocking channel for delivering a defibrillation shock pulse to the heart;
   a stimulation channel for delivering stimulation pulses to improve post-shock cardiac function;
   a controller for causing the defibrillation shocking channel to deliver a first defibrillation shock with no preceding stimulation pulses upon detection of a tachyarrhythmia from the sensed electrogram;
   wherein the controller is programmed to deliver subsequent defibrillation shocks with increasing energy until the tachyarrhythmia is terminated or a specified maximum energy is reached; and,
   wherein the controller is programmed to cause the delivery of a series of stimulation pulses to the heart prior to delivery of a subsequent defibrillation shock if the energy of the subsequent defibrillation shock is above a specified threshold and if the tachyarrhythmia has been present for a minimum specified time.

2. The device of claim 1 wherein the stimulation channel is additionally utilized as a pacing channel by the controller.

3. The device of claim 1 wherein the defibrillation shocking channel includes a pair of shock electrodes and further wherein the stimulation channel utilizes the shock electrodes for delivering stimulation pulses.

4. The device of claim 1 wherein the stimulation pulses are in a frequency range approximately between 10 and 100 Hz.

5. The device of claim 1 wherein the series of stimulation pulses delivered to the heart prior to delivery of a subsequent defibrillation shock is a pulse train of a duration on the order of 100 milliseconds to 2 seconds.

6. The device of claim 1 wherein the stimulation pulses are of a magnitude on the order of 15 to 200 volts.

7. The device of claim 1 wherein the controller is programmed to increase the energy of a subsequent defibrillation shock if a specified number of previous defibrillation shocks were unsuccessful in terminating the tachyarrhythmia.

8. A method for operating a cardiac rhythm management device, comprising:
   generating electrograms reflecting cardiac electrical activity;
   delivering a first defibrillation shock upon detection of a tachyarrhythmia from a sensed electrogram;
   delivering subsequent defibrillation shocks with increasing energy until the tachyarrhythmia is terminated or a specified maximum energy is reached; and,
   delivering of a series of stimulation pulses to the heart prior to delivery of a subsequent defibrillation shock if the energy of the subsequent defibrillation shock is above a specified threshold and if the tachyarrhythmia has been present for a minimum specified time.

9. The method of claim 8 wherein the stimulation pulses are in a frequency range approximately between 10 and 100 Hz.

10. The method of claim 8 wherein the series of stimulation pulses delivered prior to delivery of a subsequent defibrillation shock is a pulse train having a duration between 10 and 100 milliseconds.

11. The method of claim 8 wherein the stimulation pulses have an amplitude between 15 and 200 volts.

12. The method of claim 8 further comprising increasing the energy of subsequent defibrillation shocks if a specified number of previous defibrillation shocks were unsuccessful in terminating the tachyarrhythmia.

* * * * *

UNITED STATES PATENT AND TRADEMARK OFFICE
CERTIFICATE OF CORRECTION

PATENT NO. : 7,089,055 B2
APPLICATION NO. : 10/184019
DATED : August 8, 2006
INVENTOR(S) : Cates et al.

It is certified that error appears in the above-identified patent and that said Letters Patent is hereby corrected as shown below:

On the face page, in field (56), under "Foreign Patent Documents", in column 2, line 1, after "10/1981" insert -- C08F 210/02 --.

Signed and Sealed this

Nineteenth Day of December, 2006

JON W. DUDAS
*Director of the United States Patent and Trademark Office*